United States Patent
Lee et al.

(10) Patent No.: US 11,369,476 B2
(45) Date of Patent: Jun. 28, 2022

(54) FLEXIBLE ACETABULAR IMPLANT

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Stephen J. Lee, Memphis, TN (US); Jeffrey J. Shea, Memphis, TN (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 0 days.

(21) Appl. No.: 17/258,920

(22) PCT Filed: Jul. 8, 2019

(86) PCT No.: PCT/US2019/040796
§ 371 (c)(1),
(2) Date: Jan. 8, 2021

(87) PCT Pub. No.: WO2020/014119
PCT Pub. Date: Jan. 16, 2020

(65) Prior Publication Data
US 2021/0322175 A1    Oct. 21, 2021

Related U.S. Application Data

(60) Provisional application No. 62/696,479, filed on Jul. 11, 2018.

(51) Int. Cl.
*A61F 2/34* (2006.01)
*A61F 2/30* (2006.01)

(52) U.S. Cl.
CPC ............ *A61F 2/34* (2013.01); *A61F 2/30724* (2013.01); *A61F 2002/30291* (2013.01);
(Continued)

(58) Field of Classification Search
CPC .................... A61F 2/34; A61F 2/30724; A61F 2002/30291; A61F 2002/30449;
(Continued)

(56) References Cited

U.S. PATENT DOCUMENTS

| | | | |
|---|---|---|---|
| 5,314,490 | A | 5/1994 | Wagner et al. |
| 5,871,548 | A | 2/1999 | Sanders et al. |

(Continued)

FOREIGN PATENT DOCUMENTS

| | | |
|---|---|---|
| DE | 3027063 A1 | 2/1982 |
| WO | 1998015240 A1 | 4/1998 |
| WO | 2017098039 A1 | 6/2017 |

OTHER PUBLICATIONS

International Search Report and Written Opinion for International Application No. PCT/US2019/040796 dated Sep. 26, 2019.

*Primary Examiner* — Yashita Sharma
*Assistant Examiner* — Melissa A Hoban
(74) *Attorney, Agent, or Firm* — KDB Firm PLLC (57) ABSTRACT

An acetabular cage or device (100) is disclosed. In one embodiment, the acetabular cage includes a cup portion (110) configured for implantation in an acetabulum and a flange (120) extending from the cup portion. The flange including a first, bone contacting surface (126) configured to face bony tissue surrounding the acetabulum when the cup portion is implanted into the acetabulum and a second, top surface (127) opposite the first surface. The flange includes a flexible portion (130) and a fixation portion (122), the fixation portion including one or more fixation features (124) configured to facilitate fixation of the flange to the bony tissue surrounding the acetabulum. The flexible portion is arranged and configured to enable the flange, and hence the fixation portion, to move relative to the cup portion to facilitate placement of the flange relative to the bony tissue.

11 Claims, 8 Drawing Sheets

(52) U.S. Cl.
CPC ............... *A61F 2002/30449* (2013.01); *A61F 2002/3401* (2013.01); *A61F 2002/3432* (2013.01)

(58) Field of Classification Search
CPC ...... A61F 2002/3401; A61F 2002/3432; A61F 2002/30576; A61F 2002/30578; A61F 2002/3403
See application file for complete search history.

(56) References Cited

U.S. PATENT DOCUMENTS

| | | |
|---|---|---|
| 5,931,870 A | 8/1999 | Cuckler et al. |
| 6,458,161 B1 | 10/2002 | Gibbs et al. |
| 6,908,486 B2 | 6/2005 | Lewallen |
| 7,291,177 B2 | 11/2007 | Gibbs |
| 7,485,148 B2 | 2/2009 | Wozencroft et al. |
| 7,604,667 B2 | 10/2009 | DeSmet et al. |
| 7,682,399 B2 | 3/2010 | Shields et al. |
| 8,597,365 B2 | 12/2013 | Meridew |
| 9,427,320 B2 | 8/2016 | Meridew |
| 2009/0088864 A1 | 4/2009 | Lewis |
| 2016/0317308 A1 | 11/2016 | Shea |
| 2018/0140427 A1 | 5/2018 | Conway et al. |

FLEXIBLE ACETABULAR IMPLANT

CROSS-REFERENCE TO RELATED APPLICATION

This application is a United States National Phase filing of International Application No. PCT/US2019/040796, filed 8 Jul. 2019, which claims the benefit of U.S. Provisional Patent Application Ser. No. 62/696,479, filed Jul. 11, 2018, entitled Flexible Acetabular Implant, the entire contents of which applications are hereby incorporated by reference in their entirety.

FIELD OF INVENTION

The present disclosure generally relates to orthopedic implants, and more particularly but not exclusively relates to acetabular cage, device, apparatus, system, etc. (used interchangeably herein) having a flexible region or portion for facilitating improved placement.

BACKGROUND

Acetabular cage systems are typically used to address acetabular defects in which large portions of a patient's medial wall is missing. Acetabular cages generally include flanges that are generally used to secure the cage to the patient's bony tissue surrounding the acetabular defect and to provide the cage with greater stability. As a result, the flanges are typically subjected to high stresses due to anatomical loading. In addition, often times, the surgeon needs to bend the flanges so the cage is better-positioned to address the acetabular defect for the case at hand. This bending, however, subjects the flanges to additional stresses. Due to the high stresses that these flanges are subjected to, be it through surgeon's bending or repeated anatomical loading, they are common areas of fracture. For these reasons among others, there remains a need for further improvements in this technological field.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides an acetabular cage. In one embodiment, the acetabular cage comprises a cup portion configured for implantation in an acetabulum and a flange extending from the cup portion. The flange including: a first surface and a second surface opposite the first surface, the first surface arranged and configured to contact a patient's bony tissue surrounding the acetabulum when the cup portion is implanted into the acetabulum; one or more fixation features arranged and configured to couple the flange to the bony tissue surrounding the acetabulum; and a flexible region arranged and configured to enable the flange to be movable positioned relative to the cup portion.

In some embodiments, the flexible region comprises a drapable chainmail structure comprising a plurality of interlinked floating members so that the flexible region is configured to conform to an overall geometry of the bony tissue surrounding the acetabulum during use.

In some embodiments, the plurality of interlinked floating members are arranged and configured to facilitate relative movement of adjacent floating members.

In some embodiments, the chainmail structure is configured to conform to the overall geometry of the bony tissue without requiring further manual manipulation.

In some embodiments, the plurality of interlinked floating members includes a plurality of landings and a plurality of interlinked hoops connecting the plurality of landings with one another so that adjacent landings are movable with respect to one another.

In some embodiments, each of the plurality of interlinked hoops is integrally formed with a corresponding one of the landings.

In some embodiments, the plurality of interlinked hoops includes a plurality of first hoops and a plurality of second hoops, wherein each of the plurality of first hoops is connected with a corresponding one of the landings, each of the plurality of second hoops is connected to adjacent first hoops for coupling adjacent landings.

In some embodiments, the flexible region includes a plurality of solid portions and a plurality of channels; each of the solid portions positioned between adjacent channels such that the channels facilitate relative movement of adjacent solid portions.

In some embodiments, the plurality of channels extend into and/or through the flange in a transverse direction and define at least one tortuous path.

In some embodiments, the flexible region includes a plurality of flexible units, each of the plurality of flexible units including a plurality of channels and a plurality of isthmian strips, the plurality of channels being formed within the flange, the plurality of channels defining the plurality of isthmian strips.

In some embodiments, the plurality of flexible units extend between and connect the cup portion to the one or more fixation features.

In some embodiments, the plurality of channels and the plurality of isthmian strips define a tortuous path along a plane of the flange.

In some embodiments, each of the plurality of flexible units includes a portion of a first channel of the plurality of channels and a portion of a second channel of the plurality of channels, the first and second channels defining a portion of a first isthmian strip of the plurality of isthmian strips.

In some embodiments, the first and second channels are configured in a double spiral pattern such that the first isthmian strip is serpentine.

In some embodiments, the flexible region includes a plurality of channels extending into and/or through the flange in a transverse direction; and a plurality of isthmian strips defined by the plurality of channels, each of the plurality of isthmian strips positioned between adjacent channels.

In some embodiments, the plurality of isthmian strips are serpentine.

In some embodiments, the flexible region further includes at least one groove operable to receive a flowable cement, wherein the at least one groove is arranged such that a geometry of the flexible region is retained upon hardening of the flowable cement.

In some embodiments, the flexible region includes a plurality of interconnected ball and sockets.

In some embodiments, the flange includes an angular span centered about a central axis of the cup portion, wherein the angular span is at least 60 degrees.

There is provided an acetabular cage, comprising: a cup portion configured for implantation in an acetabulum; and a flange extending from the cup portion and along a plane, the flange having a first side surface configured to face bony tissue surrounding the acetabulum when the cup portion is implanted to the acetabulum, the flange having a second side surface opposite the first side surface, wherein the first side surface and the second side surface are offset from one another in a direction transverse to the plane, the flange comprising a flexible portion and one or more fixation features configured to facilitate fixation of the flange to the bony tissue surrounding the acetabulum; wherein the flexible portion includes a plurality of solid portions and a plurality of channels; wherein the solid portions are defined between the channels; and wherein the channels extend through the flange in the transverse direction and define at least one tortuous path such that the channels facilitate relative movement of adjacent segments of the solid portions, the channels facilitating said relative movement in the transverse direction and along the plane.

In some embodiments, the one or more fixation features may be connected to the cup portion via the flexible portion such that the flexible portion facilitates movement of the one or more fixation features relative to the cup portion.

In some embodiments, the flange may have an angular span centered about a central axis of the cup portion, wherein the angular span is at least 60°, wherein the fixation portion includes a plurality of the fixation features, and wherein the plurality of fixation features are angularly spaced from one another.

In some embodiments, the one or more fixation features may comprise a plurality of the fixation features, wherein a first of the fixation features is connected to a second of the fixation features via the flexible portion such that the flexible portion facilitates relative movement of the first fixation feature and the second fixation feature.

In some embodiments, the one or more fixation features may comprise at least one groove operable to receive a flowable cement, wherein the at least one groove is arranged such that the flexible is retained in a selected geometry upon hardening of the cement.

In some embodiments, a first of the solid portions may define a socket member, wherein a second of the solid portions defines a ball member, and wherein the ball member is received in the socket member such that a spheroid joint is formed between the first solid portion and the second solid portion.

There is also provided an acetabular cage, comprising: a cup portion configured for implantation in an acetabulum, the cup portion having a rim; and a flange extending from the rim, the flange having a first side configured to face bony tissue surrounding the acetabulum when the cup portion is implanted to the acetabulum, the flange having a second side opposite the first side, wherein the flange comprises a flexible portion, the flexible portion comprising a drapable chainmail structure comprising a plurality of interlinked floating members.

In some embodiments, the plurality of interlinked floating members may comprise a plurality of landings and a plurality of interlinked hoops connecting the plurality of landings with one another.

In some embodiments, one or more of the landings may comprise a porous tissue ingrowth structure formed on the first side.

In some embodiments, the chainmail structure may be configured to adopt an overall geometry of the bony tissue surrounding the acetabulum when draped over said bony tissue.

In some embodiments, the flexible portion further may comprise at least one groove operable to receive a flowable cement, wherein the at least one groove is arranged such that the chainmail structure is retained in the adopted overall geometry upon hardening of the flowable cement.

In some embodiments, the chainmail structure may be configured to adopt an overall geometry of an object over which the chainmail structure is draped.

In some embodiments, the chainmail structure may be configured to adopt said overall geometry substantially without requiring further manual manipulation.

In some embodiments, each of the hoops may be integrally formed with a corresponding one of the landings.

In some embodiments, the plurality of hoops may comprise a plurality of first hoops and a plurality of second hoops, wherein each of the first hoops is integrally formed with a corresponding one of the landings, wherein the second hoops are not integrally formed with any of the landings, and wherein the first hoops are interlinked with one another via the second hoops.

There is also provided an acetabular cage comprising a flange extending from a rim, the flange having a first side surface configured to face bony tissue surrounding the acetabulum when the cup portion is implanted to the acetabulum, the flange having a second side surface opposite the first side surface, wherein the first side surface and the second side surface are offset from one another in a transverse direction of the flange, the flange comprising: a fixation portion including one or more features configured to facilitate fixation of the fixation portion to the bony tissue surrounding the acetabulum; a flexible portion connected between the rim and the fixation portion, the flexible portion comprising a plurality of isthmian strips, wherein each of said isthmian strips extends between and connects the rim and the fixation portion; and a plurality of channels, wherein each channel extends through the flange in the transverse direction, and wherein the channels define the plurality of isthmian strips.

In some embodiments, the isthmian strips may be serpentine.

In some embodiments, the channels may form disconnected plural-spiral patterns.

In some embodiments, the plural-spiral patterns may be rectilinear.

In some embodiments, the isthmian strips may meet one another at junctions, wherein the junctions are fenestrated.

In some embodiments, one or more of the channels may include a first channel segment and a second channel segment extending from the first channel segment at an angle.

Embodiments of the present disclosure provide numerous advantages. For example, providing a flange having a flexible region or portion facilitates placement of the flange relative to the patient's bony tissue surrounding the acetabulum and thus proper positioning of the fixation region and bone screws while minimizing the associated stresses that these flanges are subjected to either through a surgeon's bending or repeated anatomical loading.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

The description herein makes reference to the accompanying figures wherein like reference numerals refer to like parts throughout the several figures and views.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings. Additionally, the description herein makes reference to the accompanying figures wherein like reference numerals refer to like parts throughout the several views.

DESCRIPTION OF THE ILLUSTRATED EMBODIMENTS

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims. That is, embodiments of an improved acetabular apparatus will now be described more fully hereinafter with reference to the accompanying drawings, in which example embodiments of the present disclosure are presented. As will be described and illustrated, in some embodiments, the improved apparatus includes an acetabular apparatus including a cup having one or more flanges. In various embodiments, as will be described in greater detail, the flanges are adapted and configured to provide increased flexibility to facilitate easier adaption of the flanges to a patient's anatomy all the while reducing the associated stresses with flexing, bending, etc. the flanges.

Figure 1:
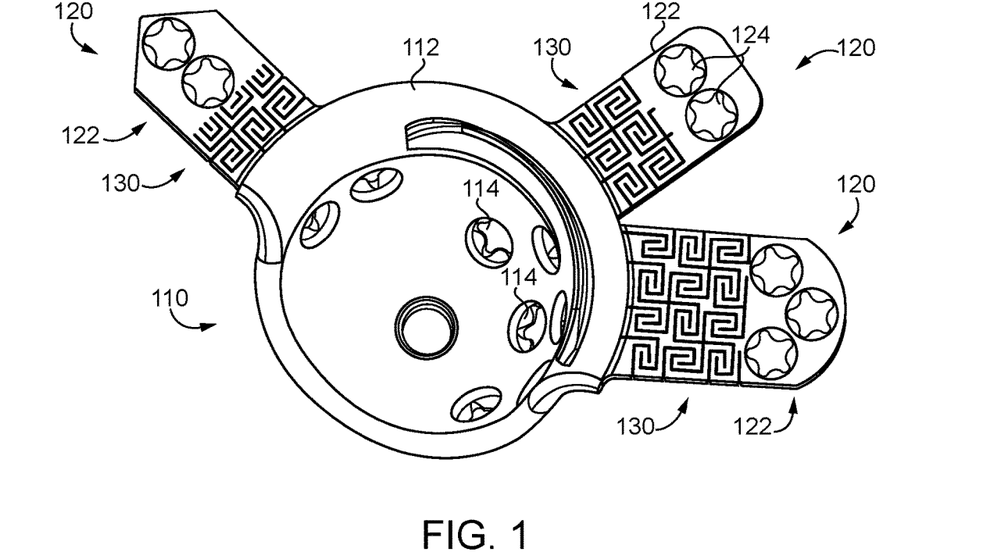
FIG. 1 is a perspective view of an example embodiment of an acetabular cage in accordance with the present disclosure.

With reference to FIG. 1, illustrated therein is an acetabular cage 100 according to certain embodiments. The acetabular cage 100 generally includes a base or cup portion 110 configured to be seated in a prepared acetabulum of a surgical patient, and one or more flanges 120 extending outwardly from a rim 112 of the cup portion 110. In use, the acetabular cage 100 may include any number of flanges including a greater or lesser number of flanges than illustrated. For example, it is envisioned that the various cages may include one, two, three, four, or more flanges. In addition, as will be shown and described, in various embodiments, the flanges may be integrally formed with the base or cup portion. However, as will be appreciated by one of ordinary skill in the art, the flanges may be separately formed and coupled to the base or cup portion by, for example, fasteners, cement, a modular mechanism, etc. Moreover, flanges may be used without any base or cup portion. In such embodiments, the flanges may be attached directly to an acetabular shell via, for example, fasteners, cement, a modular mechanism, etc.

The cup portion 110 may include one or more fastener holes 114 through which one or more fasteners such as, for example, bone screws may be passed to secure the cup portion 110 within the patient's acetabulum. The fastener holes 114 may have any appropriate shape, configuration, etc. now known or hereafter developed. For example, the fastener holes 114 may be locking or non-locking. For example, the fastener holes 114 may include a plurality of tabs for engaging a head portion of a fastener inserted therein. While the illustrated fastener holes 114 are substantially star-shaped, it is also contemplated that one or more of the fastener holes 114 may have a different geometry. For example, the fastener holes 114 may be threaded, with a single, double, or triple lead, as examples. In some embodiments, there may be two or more layers of tabs that form the star-shaped holes. While five tabs are illustrated, the star-shaped holes may have as few as three tabs or as many as eight tabs. Additional information on the operation and configuration of the tab configuration for engaging the head of the fastener in order to secure the fastener at a desired position and at a desired angular orientation within the opening can be found in U.S. Pat. No. 10,092,337 entitled Systems and Methods for Using Polyaxial Plates.

In the illustrated embodiment, as will be readily appreciated by one of ordinary skill in the art, the cup portion 110 is configured to receive a liner (not shown) that provides an articular bearing surface. During use, the liner interfaces with a head of a femoral component. In other forms, the cup portion 110 may be configured to interface with the femoral component directly, or may be configured to interface with the femoral component via a dual-mobility assembly that provides two distinct articular interfaces.

Figure 2:
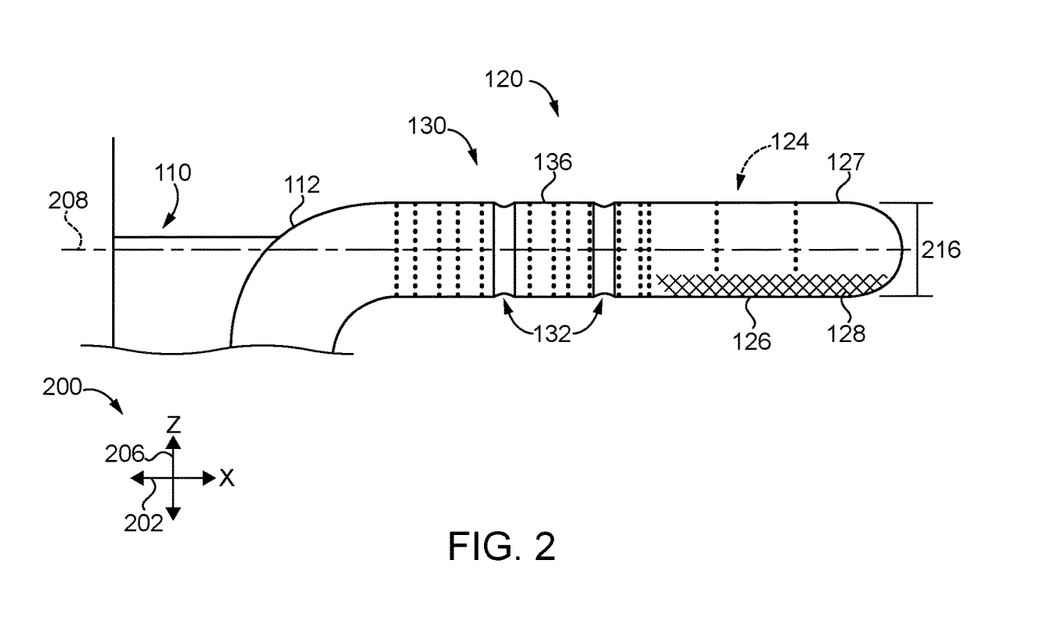
FIG. 2 is a side view of an example embodiment of a flange used in the acetabular cage of FIG. 1, the flange including a flexible structure in accordance with the present disclosure.

With additional reference to FIG. 2, the flange 120 extends outwardly from the rim 112, and in the illustrated form includes a fixation portion or region 122 and a flexible portion or region 130 (portion or region used interchangeably without the intent to limit) formed between the rim 112 and the fixation region 122. The fixation region 122 includes one or more fixation features 124 that facilitate fixation of the flange 120 to the bony tissue surrounding the patient's acetabulum. In use, the fixation features 124 are substantially similar to the fasteners holes 114 described above in connection with the cup portion 110. For example, as illustrated, the fixation feature 124 is provided in the form of a star-shaped fastener hole 125 (FIG. 3) similar to the above-described fastener hole 114. It is also contemplated that one or more of the fixation features 124 may take any other suitable form now known or hereafter developed for coupling the flange to the patient's bony tissue. By way of example, the fixation feature 124 may take the form of a recess or groove configured to receive a flowable cement, or may take the form of an opening structured to receive a pin.

The flange 120 has a bone-facing or lower side surface 126 and an opposite upper side surface 127, and a thickness dimension 216 of the flange 120 is defined as the distance between the lower and upper side surfaces 126, 127. In certain embodiments, at least a portion of the flange 120 may be provided with a porous tissue ingrowth structure 128 formed on or defining the bone-facing surface 126. While the illustrated porous tissue ingrowth structure 128 is shown confined to the fixation region 122, it is also contemplated that at least a portion of the porous tissue ingrowth structure 128 may be formed in the flexible region 130.

Figure 3:
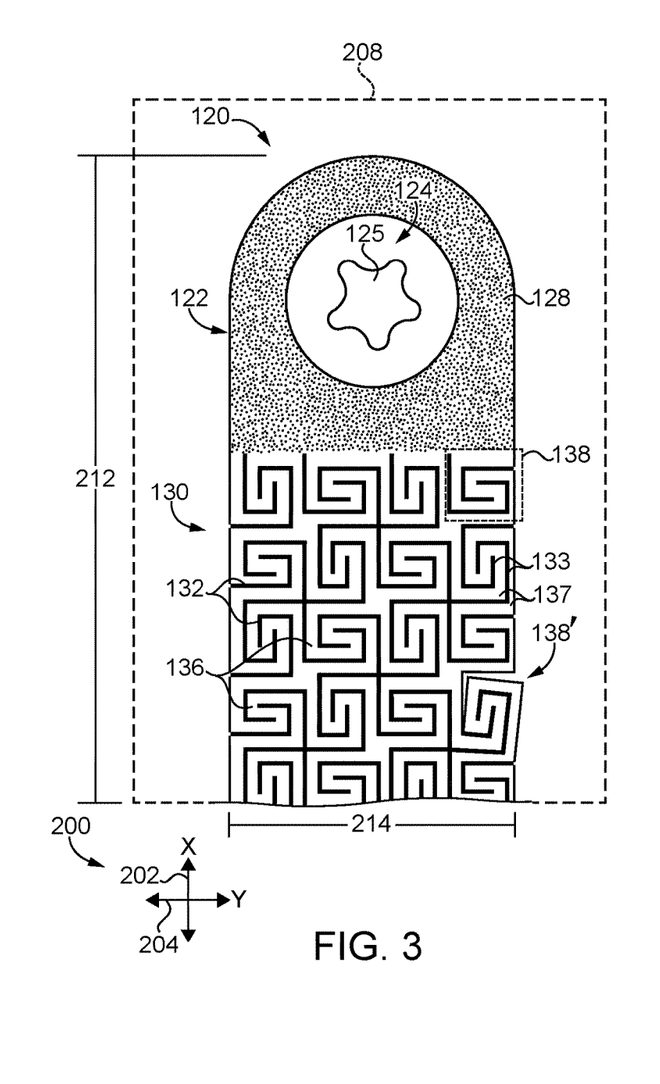
FIG. 3 is a plan view of the flange illustrated in FIG. 2.

With additional reference to FIG. 3, the flange 120 has a longitudinal length dimension 212, a lateral width dimension 214, and the transverse thickness dimension 216. As used herein, the terms "longitudinal," "lateral," and "transverse" may be used to describe directions defined by a coordinate system 200 having three mutually orthogonal axes, where the coordinate system is specific to the flange 120 being described. For example, the coordinate system illustrated in FIGS. 2 and 3 is specific to the flange 120 illustrated therein, and includes a longitudinal (X) axis 202 along which the longitudinal length dimension 212 extends, a lateral (Y) axis 204 along which the lateral width dimension 214 extends, and a transverse (Z) axis 206 along which the thickness dimension 216 extends. With the flange 120 in a standardized orientation, the flange 120 extends away from the rim 112 and along an imaginary plane 208 that includes the longitudinal (X) axis 202 and the lateral (Y) axis 204 with the transverse (Z) axis 206 being orthogonal to the plane 208.

It is to be appreciated that these terms are used for ease and convenience of description, and are without reference to the orientation of the flange 120 relative to the environment or the patient's anatomy. For example, while an element that is described as extending in a lateral direction may extend in an anatomical lateral/medial direction when the acetabular cage is implanted to the patient, such an element may additionally or alternatively extend in an anatomical superior/inferior direction and/or an anatomical anterior/posterior direction. Furthermore, extension or spacing along one direction or axis need not preclude extension or spacing along another direction or axis. For example, elements that are described as being longitudinally offset from one another may also be offset from one another in the lateral and/or transverse directions, or may be aligned with one another in the lateral and/or transverse directions. The terms are therefore not to be construed as limiting the subject matter disclosed herein to a particular orientation, or as limiting the spacing and/or extension of an element to a single direction unless specifically stated to the contrary.

In use, the flexible region 130 couples the fixation region 122 to the cup portion 110 so that the fixation region 122 can be moved relative to the cup portion 110 to facilitate better placement of the fixation region 122. As illustrated in FIG. 3, in one embodiment, the flexible region 130 includes a plurality of channels 132 formed within the flange 120. As illustrated, the channels 132 may cooperate to define a plurality of isthmian strips 136. In use, the isthmian strips 136 extend between and connect the rim 112 of the cup portion 110 and the fixation region 122. Thus arranged, the flexible region 130 includes a plurality of flexible units 138, each of which includes portions of two or more channels 132, which cooperate to define a portion of an isthmian strip 136. Each of the channels 132 includes a plurality of channel segments 133, each of the isthmian strips 136 includes a plurality of strip segments 137, and each of the strip segments 137 is defined at least in part by one or more of the channel segments 133. The channels 132 extend into and/or through the thickness dimension 216 of the flange 120 such that a channel segment 133 formed between two adjacent strip segments 137 separates the strip segments 137 from one another, thereby facilitating relative movement of the strip segments 137. For example, FIG. 3 illustrates one flexible unit 138' that has been deformed along the plane 208 by moving the strip segments 137 of the flexible unit 138' relative to one another and relative to the strip segments 137 of an adjacent flexible unit 138. While the isthmian strips 136 are illustrated as generally linear, other geometries may be used. For example, arcuate segments may be used. Further, while the channels are illustrated as generally linear, other geometries may be used. For example, a series of small holes may be used to form each channel.

Figure 4:
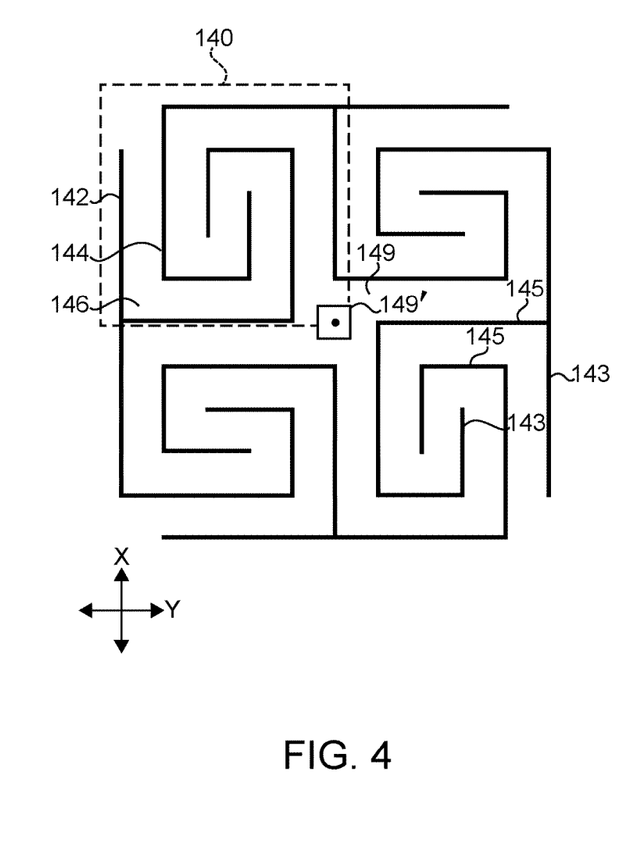
FIG. 4 is an enlarged plan view of the flexible structure illustrated in FIGS. 2 and 3.

With additional reference to FIG. 4, illustrated therein is an example flexible unit 140, which corresponds to the flexible units 138 illustrated in FIG. 3. The flexible unit 140 includes a portion of a first channel 142 and a portion of a second channel 144, which cooperate to define a portion of an isthmian strip 146. As illustrated, in one embodiment, the first and second channels 142, 144 may be generally configured in a double spiral pattern such that the isthmian strip 146 is serpentine, although other configurations are envisioned. In the illustrated embodiment, the first and second channels 142, 144 are provided in the form of disconnected rectilinear spirals, such that the isthmian strip 146 is also rectilinear. In other forms, the first and second channels 142, 144 may be curvilinear or include curvilinear portions such that the isthmian strip 146 includes one or more curvilinear edges. Furthermore, while the spiral geometries illustrated herein are double-spiral geometries, it is also contemplated that other forms of plural-spiral geometries may be utilized, such as triple-spiral geometries or quadruple-spiral geometries.

In certain forms, the flexible units 140 may be fundamental repeating structures that are replicated to define the flexible region 130. For example, FIG. 4 illustrates a pattern of four flexible units 140 in which two of the flexible units 140 are rotated 90° relative to the other two flexible units 140. As a result, the isthmian strips 146 of the flexible units 140 meet one another at a junction 149. In certain embodiments, the junction 149 may be fenestrated, for example with a window 149'.

As will be appreciated, the type of flexibility provided by a particular channel depends in part upon the orientation of the channel relative to the overall flexible portion 130. Typically, a channel segment extending in one direction within a plane will provide shear flexibility in that direction and extension flexibility in a perpendicular direction. For example, the longitudinally extending channel segments 143 provide longitudinal shear flexibility and lateral extension flexibility, whereas the laterally-extending channel segments 145 provide longitudinal extension flexibility and lateral shear flexibility. As will be appreciated, both types of channel segments also may provide for transverse shear flexibility. Thus, the geometry of the flexible portion 130 facilitates deformation of the flexible portion 130 in three dimensions, as well as bending of the flexible portion about several different rotational axes.

In the illustrated form, the first and second channels 142, 144 and the isthmian strips 146 are generally aligned with the longitudinal and lateral directions. It is also contemplated that one or more sets of first and second channels 142, 144 and isthmian strips 146 may extend at oblique angles relative to the longitudinal and lateral directions. Additionally, the illustrated longitudinal channel segments 143 run parallel to one another and perpendicular to the laterally-extending channel segments 145 such that the isthmian strips 146 are of generally constant widths. However, it is also contemplated that the width of an isthmian strip 146 may vary, for example in embodiments in which the channels defining the strip run at oblique angles relative to one another.

In the flange 120 illustrated in FIG. 3, the flexible portion 130 includes four columns and five rows of flexible units 138. As will be appreciated, the number of rows and columns appropriate for a particular flange 120 may vary based upon a number of factors, including the dimensions of the flexible units 138 and the desired dimensions of the flexible region 130. In certain embodiments, the number of rows and/or columns of units may be fractional. For example, the leftmost flange 120 illustrated in FIG. 1 includes three columns, one full row, and a portion of a second row.

While the illustrated flexible region 130 includes repeating flexible units 138, it is to be appreciated that other forms are contemplated for the flexible region 130. By way of example, the pattern defining the channels 132 and the isthmic strips 136 for one or more flexible units 138 may be subjected to a controlled randomization. As another example, the pattern defining the channels 132 and the isthmian strips 136 for the overall flexible region 130 may be subjected to controlled randomization, and repeating or modular unit sections may be omitted.

Regardless of the precise configuration of the flexible region 130, the channels 132 and the isthmian strips 136 may define tortuous paths in the plane 208 along which the flange 120 extends, and the width of each isthmian strip 136 is significantly less than the overall lateral width dimension 214 of the flange 120. As a result, each individual isthmian strip 136 has a significantly lower cross-sectional area than the flange 120 as a whole, which facilitates the deformation of the flexible region 130 to a desired geometry. Additionally, the channels 132 provide natural points of separation between the isthmian strips 136, thereby further facilitating manipulation of the isthmian strips 136 and the flange 120 as a whole. These factors among others cooperate to render the flanges 120 significantly easier for the surgeon to bend to a desired shape that conforms to the patient's anatomy, and may further increase the fidelity with which the deformed flexible portion or region 130 conforms to the overall geometry of that the selected bone surface. For example, during implantation, the flexibility of the flexible region 130 as a result of the channels 132 and isthmian strips 136 facilitates the manual manipulation of the flexible region 130 to a geometry that conforms to that of the object on which it is positioned. That is, during implantation, in order to facilitate positioning of the flange relative to base or cup portion (e.g., positioning of the fixation region 122) manual manipulation of the flexible region is needed (force of gravity is generally insufficient to cause the flexible region to adopt to the overall geometry of the patient). This characteristic of facilitated deformation may be referred to herein as pliability, and flexible structures exhibiting such pliability may be referred to herein as pliable.

Figure 5:
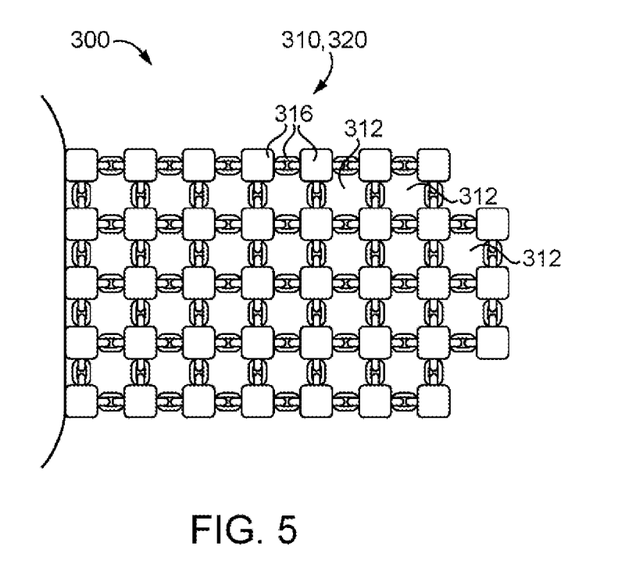
FIG. 5 is a plan view of an alternate embodiment of a flexible structure used in a flange in accordance with the present disclosure.

With reference to FIG. 5, an alternate example embodiment of a flange 300 having a flexible region 310 according to certain embodiments is shown. Like the above-described flexible region 130, the flexible region 310 includes solid portions 316 having openings or channels 312 formed therebetween to facilitate relative movement of the solid portions 316. In the current embodiment, however, the solid portions 316 are provided in the form of interlinked floating members 316 that define a chainmail structure 320. As described herein, the solid portions or floating members 316 are generally disconnected from one another such that relative movement of the floating members 316 is permitted, but are interlinked with one another such that the relative movement of adjacent floating members 316 is limited.

Figure 6:
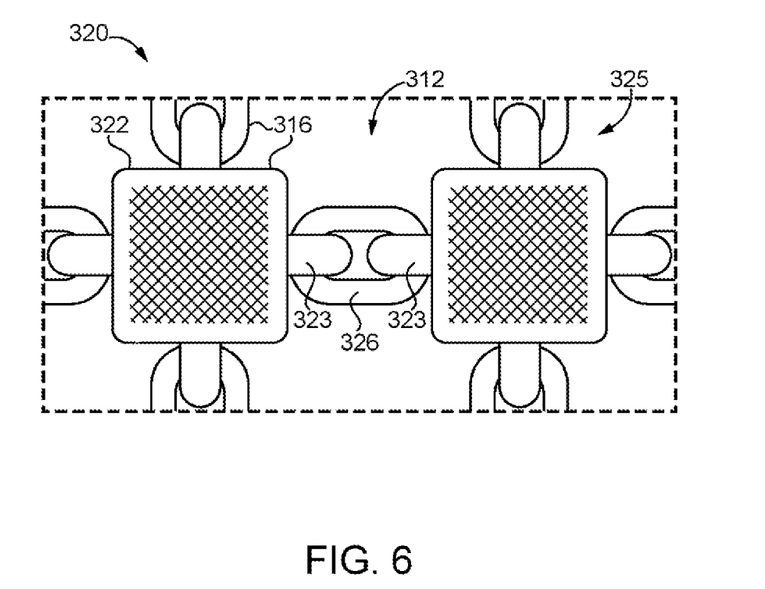
FIG. 6 is an enlarged plan view of the flexible structure illustrated in FIG. 5.
Figure 7:
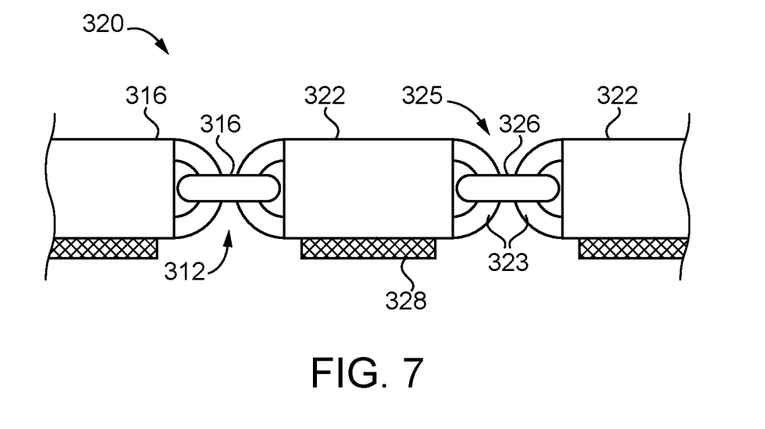
FIG. 7 is an enlarged side view of the flexible structure illustrated in FIGS. 5 and 6.

The floating members 316 may be coupled to each other by any suitable mechanism now known or hereafter developed to facilitate relative movement between the floating members 316 so that the flexible region 310 enables relative movement of the fixation region relative to the cup portion. For example, with additional reference to FIGS. 6 and 7, which illustrate additional views of the chainmail structure 320 illustrated in FIG. 5, the chainmail structure 320 may include a plurality of landings 322 and a plurality of interlinked hoops 325 by which the landings 322 are linked to one another. Each landing 322 includes a plurality of base hoops 323, each of which faces a base hoop 323 of an adjacent landing 322. The base hoops 323 of adjacent landings 322 are linked to one another via one or more floating hoops 326, which are not necessarily formed on landings 322. As a result, relative movement of the interlinked floating members 316 is permitted, but is restricted to a limited range.

Figure 8:
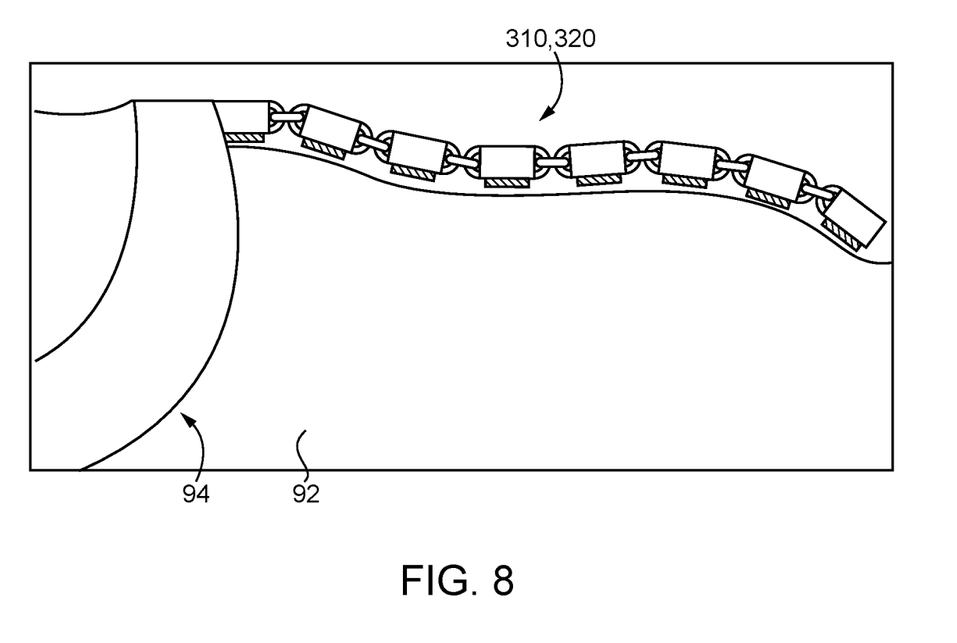
FIG. 8 is a cross-sectional view of the flexible structure illustrated in FIG. 5 draped over bony tissue surrounding an acetabulum.

With additional reference to FIG. 8, the disconnected but interlinked nature of the floating members 316 provides the flexible region 310 with a different type of flexibility as compared to the flexibility provided by the isthmian strips 136 of the above-described flexible region 130. More specifically, the fact that the floating members 316 are in a sense disconnected from one another enables some free movement of the floating members 316 without requiring deformation of the material. Thus, when the chainmail structure 320 is draped over an object, such as the bony tissue 92 surrounding the acetabulum 94, the force of gravity causes the chainmail structure 320 to adopt the overall geometry of the flexible region 310 substantially without requiring further manual manipulation. This characteristic may be referred to herein as drapability, and flexible structures exhibiting such a characteristic may be referred to herein as drapable.

In the illustrated embodiment, each channel 312 is substantially straight such that the landings 322 are substantially square. However, due to the interconnected nature of the channels 312, the channels, when taken together, define tortuous paths within the plane along which the flange 300 extends when in the standard orientation. Furthermore, it is to be appreciated that the landings 322 may have different arrangements and/or geometries from those illustrated in the Figures. As one example, square landings may be offset from one another to provide for channels that exhibit a step-like geometry. As another example, the landings may be provided with a hexagonal geometry such that the channels exhibit a honeycomb-like geometry. In further embodiments, the landings 322 may be omitted from one or more portions of the chainmail structure 320 such that that portion is comprised entirely of interlinked floating hoops 326.

In addition to contributing to the drapability of the chainmail structure 320, the channels 312 may serve additional functions that facilitate the implantation of an acetabular cage including the flange 300. For example, once the flexible region 310 has been draped over the target surface and adopted the geometry thereof, a flowable cement may be introduced to the channels 312. Upon hardening, the cement locks the previously flexible chainmail structure 320 in the desired configuration, and may further aid in securing the flange 300 to the bony tissue surrounding the acetabulum. Thus, the channels 312 themselves may be considered to define fixation features configured to facilitate fixation of the flange 300 to the bony tissue surrounding the acetabulum.

Figure 9:
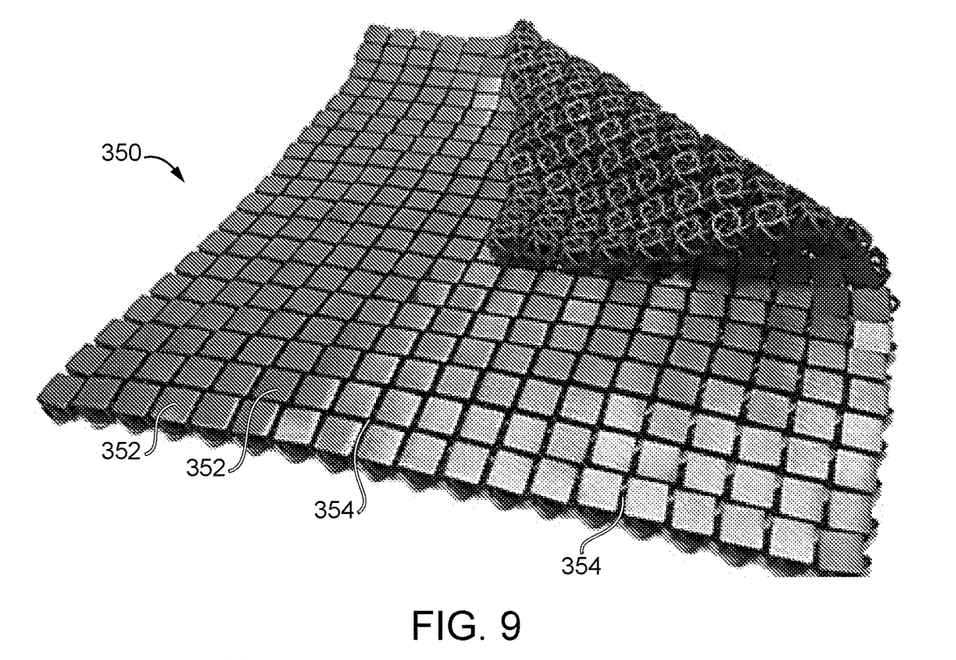
FIG. 9 is a perspective view of an alternate embodiment of a flexible structure that may be utilized to form a flexible region of a flange in accordance with the present disclosure.
Figure 10:
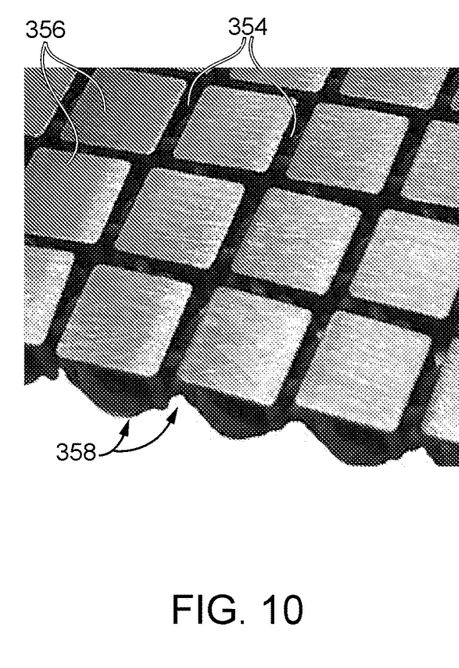
FIG. 10 is a top, detailed view of the flexible structure illustrated in FIG. 9.
Figure 11:
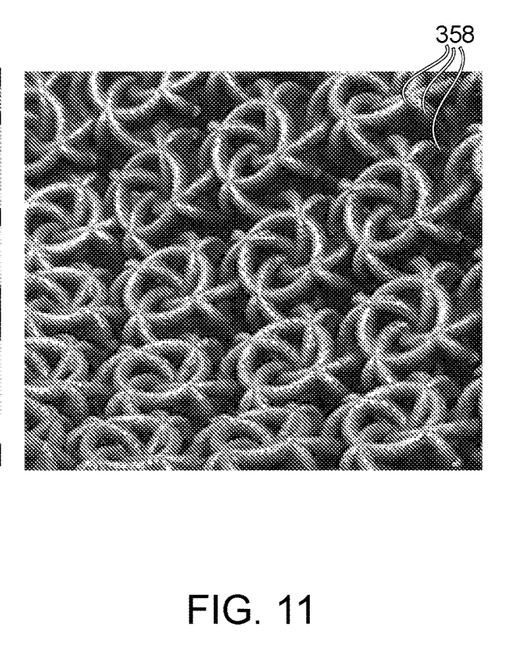
FIG. 11 is a bottom, detailed view of the flexible structure illustrated in FIG. 9.

With reference to FIGS. 9-11, an alternate embodiment of a chainmail structure 350 that may be utilized to form a drapable portion of a flange is illustrated. Like the above-described chainmail structure 320, the illustrated chainmail structure 350 includes a plurality of interlinked floating members 352 having channels 354 defined therebetween. As illustrated, the floating members 352 include landings 356, which may have a porous tissue ingrowth structure formed on the bone-facing sides thereof. Formed on the opposite side of the landings 356 (e.g., bone-facing side of the landings 356) are hoops 358 that interlink the floating members 352 such that the chainmail structure 350 is drapable. In contrast to the above-described chainmail structure 320, however, the chainmail structure 350 does not necessarily include floating hoops. Instead, each of the hoops 358 may be integrally formed with a corresponding one of the landings 356, and the hoops 358 of adjacent landings 356 are directly interlinked with one another.

Figure 12:
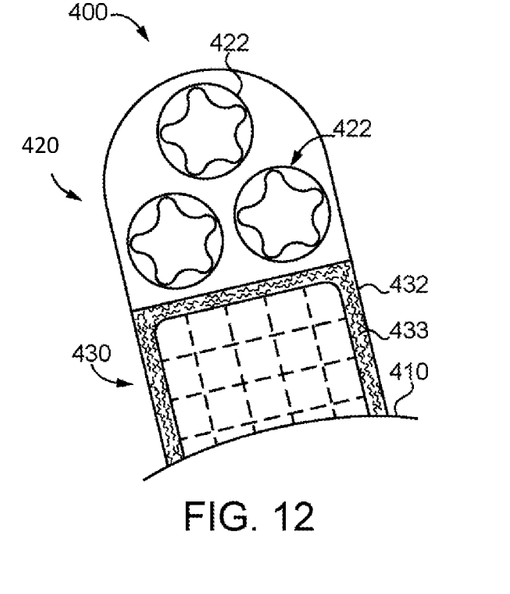
FIG. 12 is a plan view of an alternate example embodiment of a flange in accordance with the present disclosure.
Figure 13:
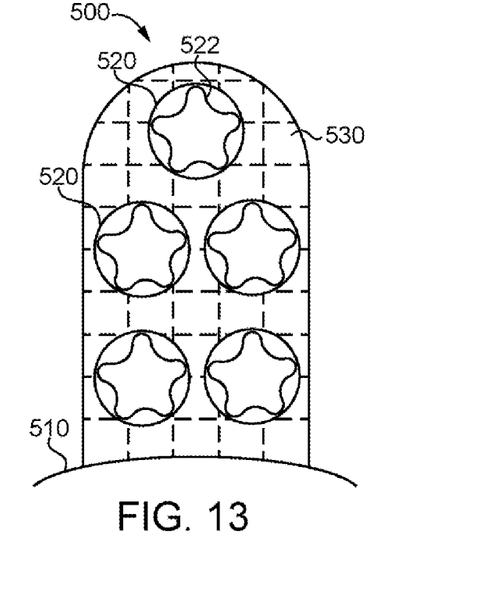
FIG. 13 is a plan view of an alternate example embodiment of a flange in accordance with the present disclosure.
Figure 14:
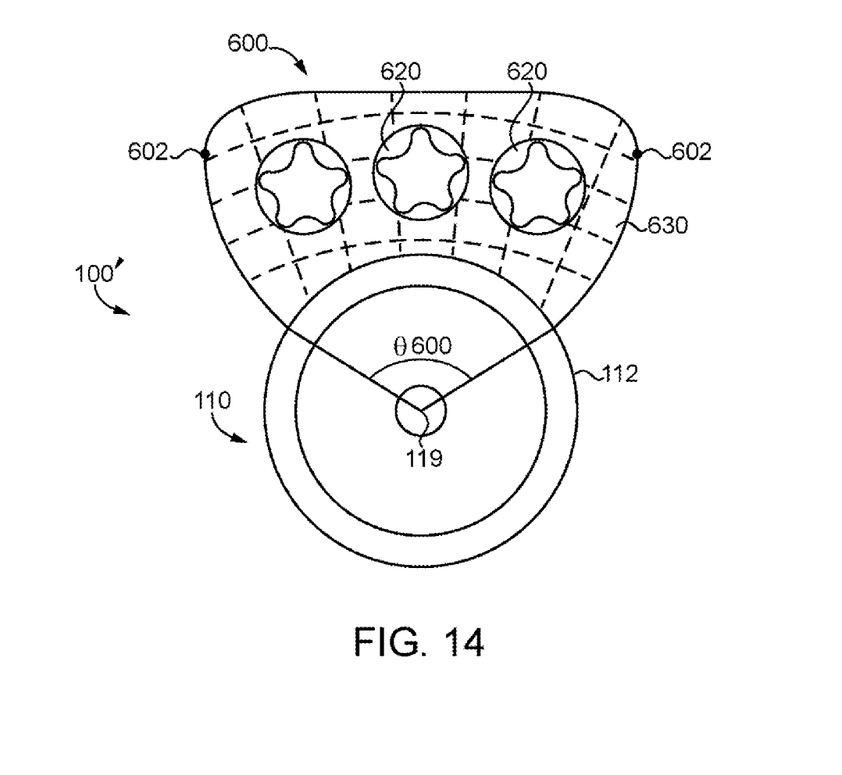
FIG. 14 is a plan view of an alternate example embodiment of an acetabular cage in accordance with the present disclosure.

With reference to FIGS. 12-14, alternate embodiments of acetabular cages according to present disclosure are illustrated. Each of the acetabular cages generally includes a base or cup portion 110 and one or more flanges extending therefrom, each of the flanges including a flexible region. In FIGS. 12-14, the flexible regions are generally indicated with a pattern of dashed lines, where the dashed lines schematically represent openings or channels that extend into and/or through the thickness of the flange. It is to be appreciated that the configurations of the flexible regions are not intended to be limited to the schematic representations thereof, and that such flexible regions may take any of a number of forms. In certain forms, the flexible regions may be provided as a pliable region, such as the pliable regions described with reference to FIGS. 1-4. In other embodiments, the flexible regions may be provided as a drapable region, such as the drapable regions described with reference to FIGS. 5-11. It is further contemplated that a flexible region may include both pliable regions and drapable regions. As such, the flexible regions described hereinafter are to be understood as not being limited to the particular patterns illustrated in the Figures.

Additionally, as previously described, each of the flanges described hereinafter may include one or more fixation features that facilitate the fixation of the flange to the bony tissue surrounding the acetabulum. While the fixation features are illustrated in the Figures as being provided in the form of star-shaped openings, it is to be appreciated that other forms of fixation features may be utilized. By way of example, one or more fixation features may take the form of a threaded opening for receiving a threaded fastener. Alternatively, one or more fixation features may take the form of a recess or groove configured to receive a flowable cement, or may take the form of an opening structured to receive a fixation pin. As such, the fixation features referred to hereinafter are to be understood as not being limited to the particular features illustrated in the Figures.

With reference to FIG. 12, illustrated therein is a flange 400 according to certain embodiments. The flange 400 extends from a rim 410 and generally includes a fixation region 420 and a flexible region 430 connecting the rim 410 with the fixation region 420. The fixation region 420 includes one or more fixation features 422 configured to facilitate fixation of the flange 400 to the bony tissue surrounding the acetabulum. In the illustrated form, the fixation region 420 is substantially rigid, and resists relative movement of the fixation features 422. It is also contemplated that the fixation region 420 may include one or more flexible portions, for example as described below with reference to FIG. 13. In such forms, the additional flexible portions may facilitate relative movement of the fixation features 422.

In addition to a flexible structure such as any of those described herein, the flexible region 430 may also include a fixation feature in the form of a channel or groove 432. The groove 432 is configured to receive a flowable cement 433 which, upon hardening, at least partially locks the flexible region 430 in the selected configuration. In the illustrated form, the groove 432 and the rim 410 cooperate to generally surround the flexible region 430 such that upon hardening of the cement 433, the outer boundary of the flexible region 430 becomes fixed, while the flexible region 430 remains flexible in the transverse direction. In other forms, one or more grooves may be arranged such that upon hardening of the cement, the geometry of the flexible region 430 is fixed. For example, such grooves may be connected to the channels of the flexible region 430 such that the flowable cement infiltrates the channels and freezes the overall geometry of the flexible region 430. It is also contemplated that the groove 432 may be disconnected from the channels to discourage infiltration of the cement into the channels. For example, in embodiments in which the flexible region 430 includes a porous tissue ingrowth structure, it may be undesirable to have the cement infiltrate the tissue ingrowth structure, and the groove 432 may remain disconnected from the channels to discourage such infiltration.

With reference to FIG. 13, illustrated therein is a flange 500 according to certain embodiments. The flange 500 extends from a rim 510 and generally includes an integrated region that includes a plurality of fixation regions 520 and a flexible region 530. In use, each fixation region 520 is substantially solid to provide for increased structural strength, which also renders the fixation regions 520 substantially rigid. However, the fixation regions 520 are connected to one another via the flexible region 530 (e.g., the fixation regions 520 may be dispersed within the flexible region 530), which facilitates relative movement of the fixation regions 520. As a result, the position and/or orientation of the fixation regions 520 can be independently adjusted, for example to more fully seat against a desired portion of the bony tissue surrounding the acetabulum.

With reference to FIG. 14, illustrated therein is an acetabular cage 100' according to certain embodiments. The acetabular cage 100' includes a base or cup portion 110 having a rim 112 such as those previously described herein. In addition, the cage 100' includes a flange 600. Like the above described flange 500, the flange 600 may include a plurality of fixation regions 620 dispersed within a flexible region 630 for connecting the fixation regions 620 to the cup portion 110. However, in contrast to previously described flanges, the flange 600 has a significantly greater angular span θ600 than the above-described flanges such that the flange 600 spans at least the majority of that portion of the rim that faces the anatomical superior direction when the acetabular cage 100' is implanted to the patient. The angular span θ600 is measured as the central angle subtended by the flange 600 relative to the central axis 119 of the cup portion 110. In the illustrated form, the angular span θ600 is defined at the rim 112, is greater than 90°, and more specifically is about 120°. It is also contemplated that the angular span θ600 may be measured relative to another set of end points of the flange 600, such as the points 602 at which the lateral width of the flange 600 is greatest. In such forms, the angular span θ600 may be 90° or less. In either event, the angular span θ600 may be greater than 60° to provide for suitable coverage of the bony tissue surrounding the acetabulum. While FIG. 14 illustrates and describes a flange similar to flange 500, it is envisioned that flange 600 may be arranged and configured with fixation regions 620 and flexible regions 630 similar to those of other described embodiments. For example, the flexible region may include a chainmail structure, a plurality of channels and isthmian strips, etc.

Figure 15:
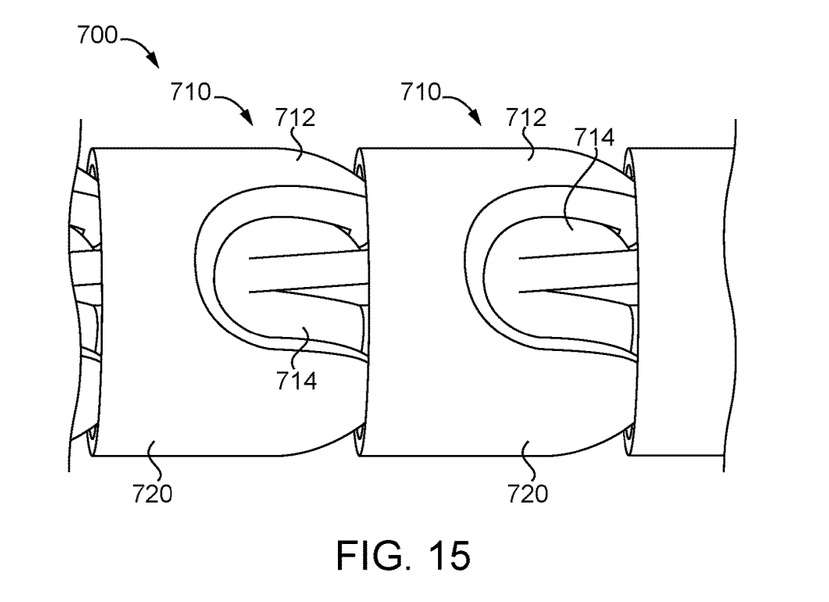
FIG. 15 illustrates an alternate example embodiment of a flexible structure in accordance with the present disclosure.
Figure 16:
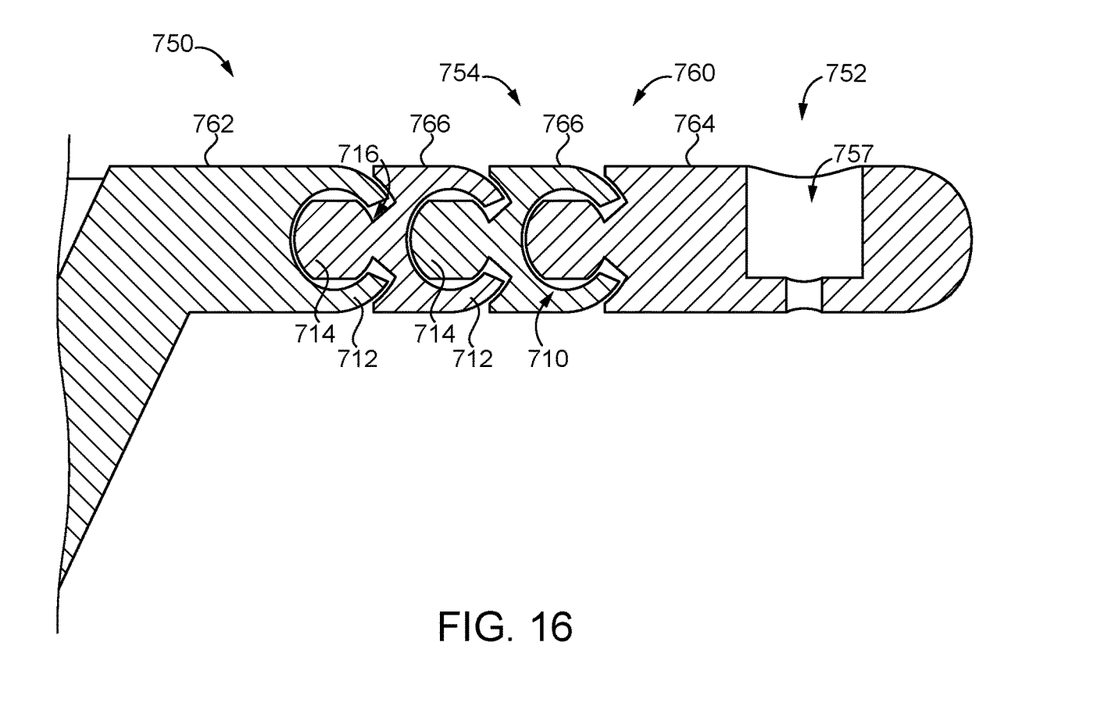
FIG. 16 is a cross-sectional view of an example embodiment of a flange including the flexible structure illustrated in FIG. 15.

With reference to FIGS. 15 and 16, illustrated therein is an alternate example embodiment of a flexible structure 700. As illustrated, the flexible structure 700 is provided in the form of a ball-and-socket structure 700 including one or more spheroid joints 710. The ball-and-socket structure 700 may also be referred to herein as the spheroid joint structure 700. Each joint 710 includes a socket member 712 and a ball member 714 pivotably received in the socket member 712. As will be readily appreciated by one of ordinary skill in the art, the ball-and-socket structure enables relative movement of the fixation region 752 located on one side of the ball-and-socket structure relative to the base or cup portion located on the other.

In one embodiment, each joint 710 is defined by two links 720, one of which defines the socket member 712 and the other of which defines the ball member 714. The socket member 712 is disconnected from the ball member 714 such that a tortuous channel 716 extends through the thickness of the structure 700.

Referring to FIG. 16, the flange 750 includes a fixation region 752 that is connected to the rim of the cup via a flexible region 754 that includes the spheroid joint structure 700. The joint structure 700 includes a plurality of links 760 that includes a base link 762 and an end link 764, and which may further include one or more intermediate links 766. The base link 762 is formed at the rim of the cup, and the end link 764 defines at least a portion of the fixation region 752 and includes a fixation feature 757 in the form of an opening.

Each of the links 760 includes a socket member 712 and/or a ball member 714. In the illustrated form, the base link 762 includes a socket member 712, the end link 764 includes a ball member 714, and each of the intermediate links 766 includes both a socket member 712 and a ball member 714. However, it is to be appreciated that other forms are contemplated. For example, the base link 762 may include a ball member and/or the end link 764 may include a socket member. As another example, one or more intermediate links 766 may include two ball members, each of which is engaged with a socket member of an adjacent link. As a further example, one or more intermediate links 766 may include two socket members, each of which is engaged with a ball member of an adjacent link.

In the illustrated form, the flexible region 754 is formed of one or more spheroid joint structures 700. By way of example, several of the structures 700 may be positioned next to one another to define strands that extend between and connect the cup portion (e.g., rim) and the fixation region 752. In certain forms, the strands may be disconnected such that the strands are free to move relative to one another. In other forms, a link of one strand may be integral with a link of an adjacent strand such that the strands move at least partially in unison.

In certain embodiments, a spheroid joint structure may be used in combination with another form of flexible structure. By way of example, a line of spheroid joints 710 may be formed at the rim, and may connect the rim with a flexible structure such as the flexible region 130. In such forms, each joint 710 may, for example, be associated with a corresponding and respective isthmian strip. In other embodiments, the line of spheroid joints may form one or more hinges such that one or more of the end links 764 is directly engaged with a corresponding base link 762.

As is evident from the foregoing, the flanges described herein are capable of providing greater flexibility than conventional flanges, which facilitates the process of conforming the flanges to the bony tissue surrounding the acetabulum. This flexibility may also increase the fidelity with which the flange conforms to the bony tissue, which may improve long-term outcomes for the patient.

Additionally, the flexibility of the flexible structures described herein is due at least in part to the geometry of those structures. As a result, these flexible structures may be formed of materials having greater strength than those typically employed in flanges for which flexibility is desired. For example, certain conventional acetabular cages include flanges that are formed of commercially pure titanium, which has a lower strength and is thus more flexible than certain titanium alloys. While the structures described herein can be formed of such commercially pure titanium, the geometry-based flexibility of the structures may enable the structures to retain the desired degree of flexibility when formed of a stronger material, such as a titanium alloy. Such stronger materials will typically exhibit increased resistance to wear, which may further improve long-term outcomes for the patient.

In certain embodiments, the flexible structures described herein may be manufactured according to conventional techniques, such as those that involve forging, stamping, and/or fusing. In other forms, the flexible structures may be manufactured according to additive manufacturing techniques, such as selective laser sintering (SLS) or direct metal laser sintering (DMLS). One advantage of such additive manufacturing techniques is the capability to create complex structures that may not necessarily be feasible with traditional techniques. For example, while the chainmail structure illustrated in FIGS. 8-10 and/or the ball and socket structure illustrated in FIGS. 15 and 16 may be difficult or infeasible to manufacture with conventional techniques, such structures can often be additively manufactured with relative ease. Additionally, the orthopaedic implant may be a unitary or integral structure. In other words, the entire structure may be formed with additive manufacturing techniques, or components may be made first and form a substrate on which portions of the structure is additively manufactured.

Figures 17, 18:
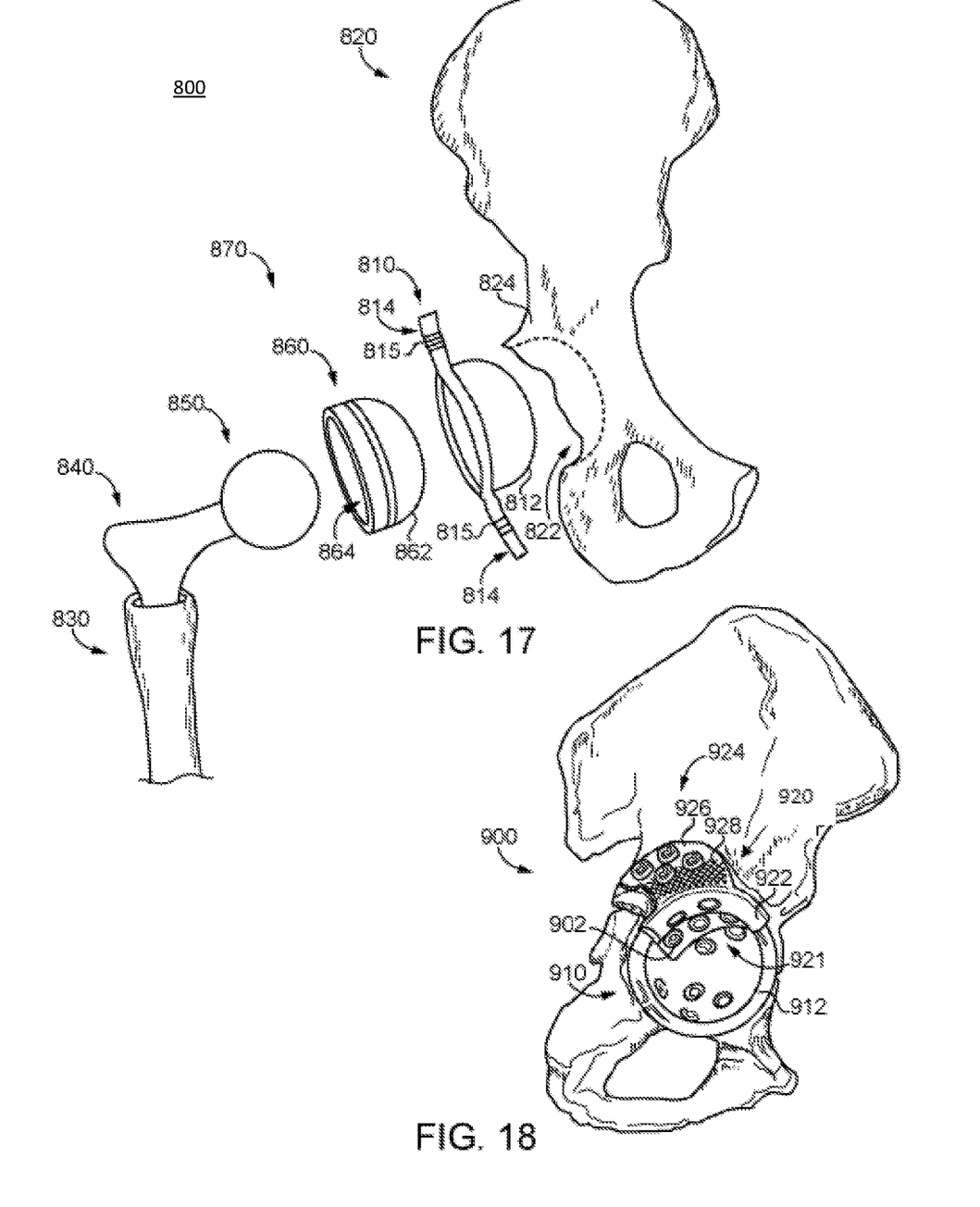
FIG. 17 is an exploded, perspective view of an example embodiment of a use case scenario involving an acetabular cage in accordance with the present disclosure.
FIG. 18 is a perspective view of an example embodiment of a system in accordance with the present disclosure.

With reference to FIG. 17, illustrated therein is an example use case scenario 800 involving an acetabular cage 810 according to certain embodiments. The cage 810 includes a cup portion 812 and at least one flange 814 extending from the cup portion 812. Each flange 814 includes a flexible structure 815 that may, for example, be provided as one or more of the flexible structures disclosed herein. The cage 810 is configured for implantation to a hip 820 having an acetabulum 822 which is surrounded by bony tissue 824. More particularly, the cup portion 812 is configured to be seated in the acetabulum 822, and the flanges 814 are configured to engage the bony tissue 824 when the cup portion 812 is seated in the acetabulum 822. Additionally, the flexible structures 815 provide the flanges 814 with a degree of flexibility that facilitates the process of conforming the flanges 814 to the irregular shape of the bony tissue 824, thereby increasing the area of contact between the flange 814 and the bony tissue 824. This increased area of contact may facilitate the fixation of the flanges 814 to the bony tissue 824, for example when such fixation involves the use of cement or tissue ingrowth into a porous structure formed on the bone-facing side of the flange 814.

In the use case scenario 800, the femur 830 of the patient has been resected, and the proximal end portion of the femur 830 has been replaced with a prosthetic hip stem 840 having a femoral head component 850 mounted thereon. Disposed between the acetabular cage 810 and the femoral head component 850 is a liner 860. The liner 860 has an outer surface 862 configured to be seated in the cup portion 812 of the cage 810, and to couple with the inner surface of the cup portion 812. By way of example, the outer surface 862 of the liner 860 may have a first engagement feature, such as a ridge and/or a groove, and the inner surface of the cup portion 812 may have a mating engagement feature, such as a groove and/or a ridge. The liner 860 also has an inner bearing surface 864 configured to receive the femoral head component 850 such that the outer surface of the femoral head component 850 and the inner bearing surface 864 define an articular interface. In certain embodiments, the cage 810, the hip stem 840, the femoral head component 850, and the liner 860 may be provided in a kit 870.

Additionally, while the flexible structures have been illustrated as being integrally formed with the cup portion, it is to be appreciated that other forms are contemplated. By way of example, a "cup-cage" technique may be utilized, in which the cup portion and the flexible flanges are formed as distinct and separable components. In such forms, the cup portion may be provided as a conventional acetabular cup, and one or more separate components including the flexible flange or flanges may be secured to the cup by any suitable mechanism now known or hereafter developed including, for example, using fasteners such as screws, cement, etc.

With additional reference to FIG. 18, illustrated therein is an acetabular cup-cage system 900 according to certain embodiments. The system 900 generally includes a cup portion 910 and a cage portion 920 that is separate and distinct from the cup portion 910. The cup portion 910 may, for example, be a conventional acetabular cup having a generally hemispherical geometry. The cage portion 920 includes a base 921 that is configured to conform to the internal geometry of the cup portion 910. The cage portion 920 may be secured to the cup portion 910 using fasteners such as screws 902. When so secured, a rim 922 of the cage portion 920 is adjacent and abuts the rim 912 of the cup portion 910. The cage portion 920 further includes a flange 924 that extends from the rim 922, and which includes a fixation region 926 and at least one flexible region 928 connecting the rim 922 with the fixation region 926. The flange 924 may, for example, be substantially similar to one or more the flanges described hereinabove.

In the illustrated embodiment, the rim 922 of the cage portion 920 is solid and conforms closely to the geometry of the rim 912 of the cup portion 910. Additionally, the boundary between the flexible region 928 and the solid portion of the cage rim 922 is curved, and more particularly exhibits a curvature that corresponds to that of the cup rim 912. As a result, the cage portion 920 exhibits structural rigidity in those regions that abut the cup rim 912 while increasing the flexibility of those regions that do not abut the cup rim 912.

While the flexible structures are illustrated herein as being incorporated into an acetabular cage, it is to be appreciated that the flexible structures described herein may be incorporated into other orthopaedic implants. As examples, the flexible structures could be incorporated into the glenoid portion of a shoulder implant or bone plate for trauma or spinal applications.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein. The phrases "at least one", "one or more", and "and/or", as used herein, are open-ended expressions that are both conjunctive and disjunctive in operation. For example, each of the expressions "at least one of A, B and C", "at least one of A, B, or C", "one or more of A, B, and C", "one or more of A, B, or C"

and "A, B, and/or C" means A alone, B alone, C alone, A and B together, A and C together, B and C together, or A, B and C together.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. All rotational references describe relative movement between the various elements. Connection references (e.g., engaged, attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order and relative sizes reflected in the drawings attached hereto may vary.

We claim:

1. An acetabular cage, comprising:
    a cup portion configured for implantation in an acetabulum; and
    a flange extending from the cup portion, the flange including:
    a first surface and a second surface opposite the first surface, the first surface arranged and configured to contact a patient's bony tissue surrounding the acetabulum when the cup portion is implanted into the acetabulum;
    one or more fixation features arranged and configured to couple the flange to the bony tissue surrounding the acetabulum; and
    a flexible region arranged and configured to enable the flange to be moveably positioned relative to the cup portion, the flexible region including a plurality of flexible units, each of the plurality of flexible units including a plurality of channels and an isthmian strip, wherein the plurality of channels extend from the first surface to the second surface, the plurality of channels include a first linear channel and a second linear channel extending parallel to but spaced from the first linear channel, each of the first and second linear channels including a first portion and a second portion angled relative to the first portion, the isthmian strip positioned between the first and second linear channels.

2. The acetabular cage of claim 1, wherein the isthmian strip includes a plurality of solid portions positioned between adjacent channels such that the channels facilitate relative movement of adjacent solid portions.

3. The acetabular cage of claim 2, wherein at least one of the first and second linear channels extend in a transverse direction.

4. The acetabular cage of claim 1, wherein the plurality of flexible units extend between and connect the cup portion to the one or more fixation features.

5. The acetabular cage of claim 1, wherein the plurality of channels and the isthmian strip define a tortuous path along a plane of the flange.

6. The acetabular cage of claim 1, wherein the first and second linear channels are configured in a double spiral pattern such that the isthmian strip is serpentine.

7. The acetabular cage of claim 1, wherein the isthmian strip is defined by the plurality of channels, the isthmian strip positioned between adjacent channels.

8. The acetabular cage of claim 7, wherein the isthmian strip is serpentine.

9. The acetabular cage of claim 1, wherein the flexible region further includes at least one groove operable to receive a flowable cement, wherein the at least one groove is arranged such that a geometry of the flexible region is retained upon hardening of the flowable cement.

10. The acetabular cage of claim 1, wherein the flange includes an angular span centered about a central axis of the cup portion, wherein the angular span is at least 60 degrees.

11. An acetabular cage, comprising:
    a cup portion configured for implantation in an acetabulum; and
    a flange extending from the cup portion, the flange including:
    a first surface and a second surface opposite the first surface, the first surface arranged and configured to contact a patient's bony tissue surrounding the acetabulum when the cup portion is implanted into the acetabulum;
    one or more fixation features arranged and configured to couple the flange to the bony tissue surrounding the acetabulum; and
    a flexible region arranged and configured to enable the flange to be movably positioned relative to the cup portion, the flexible region including a plurality of flexible units, each of the plurality of flexible units including a plurality of channels and an isthmian strip, wherein the plurality of channels extend from the first surface to the second surface, the plurality of channels include a first channel and a second channel spaced from the first channel, the isthmian strip positioned between the first and second channels, the first and second channels being configured in a double spiral pattern such that the isthmian strip is serpentine.

* * * * *